(12) United States Patent
Goumas

(10) Patent No.: US 6,953,441 B2
(45) Date of Patent: Oct. 11, 2005

(54) PREFORMED BRACE FOR TREATING METACARPAL FRACTURES AND METHOD OF TREATING METACARPAL FRACTURES

(76) Inventor: Douglas M. Goumas, 6 Esther Dr., Bedford, NH (US) 03110

(*) Notice: Subject to any disclaimer, the term of this patent is extended or adjusted under 35 U.S.C. 154(b) by 36 days.

(21) Appl. No.: 10/645,109

(22) Filed: Aug. 21, 2003

(65) Prior Publication Data

US 2004/0039315 A1 Feb. 26, 2004

Related U.S. Application Data

(60) Provisional application No. 60/405,627, filed on Aug. 22, 2002.

(51) Int. Cl.[7] .................................................. A61F 5/00
(52) U.S. Cl. .............................. 602/7; 602/21; 602/22; 128/879; 128/880
(58) Field of Search ................................ 602/7, 21, 22, 602/62, 63, 64, 901, 20; 128/878, 879, 880, 898, DIG. 15

(56) References Cited

U.S. PATENT DOCUMENTS

| | | | | |
|---|---|---|---|---|
| 4,370,976 A | * | 2/1983 | Wanchik et al. | ............... 602/22 |
| 4,384,571 A | | 5/1983 | Nuzzo et al. | |
| 4,662,364 A | | 5/1987 | Viegas et al. | |
| 5,058,576 A | | 10/1991 | Grim et al. | |
| 5,069,203 A | * | 12/1991 | Anderson | ..................... 602/21 |
| 5,254,078 A | * | 10/1993 | Carter et al. | .................. 602/21 |
| 5,766,142 A | * | 6/1998 | Hess | ............................ 602/22 |
| 5,772,620 A | * | 6/1998 | Szlema et al. | ................. 602/21 |
| 5,916,186 A | * | 6/1999 | Turto et al. | .................... 602/20 |
| 6,120,471 A | * | 9/2000 | Varn | ........................... 602/21 |
| 6,165,148 A | * | 12/2000 | Carr-Stock | .................... 602/21 |
| 6,261,253 B1 | * | 7/2001 | Katzin | ......................... 602/21 |
| 6,681,772 B2 | * | 1/2004 | Atwater et al. | ............. 128/878 |
| 6,692,453 B2 | * | 2/2004 | Wolfe | .......................... 602/21 |
| 2002/0002348 A1 | | 1/2002 | Wiggins et al. | |

OTHER PUBLICATIONS

AliMed Inc. catalog pp. F3, F4, F5 and F12, illustrations of immobilizers, date unknown.

* cited by examiner

Primary Examiner—Fadi H. Dahbour
(74) Attorney, Agent, or Firm—Lipsitz & McAllister, LLC

(57) ABSTRACT

A preformed metacarpal fracture brace is provided in accordance with one example embodiment of the invention. The brace comprises a one-piece semi-rigid molded outer shell contoured to conform to an outside portion of a wrist and hand of a wearer. The outer shell may comprise a proximal section adapted to immobilize the wrist in an extension position and a distal section extending at an angle to the proximal section and adapted to immobilize at least the fourth and fifth metacarpals of the hand in a functional position at that angle. A soft inner shell may be applied to an inside portion of the outer shell. A plurality of straps connected to the outer shell may be provided to secure the brace onto the wearer.

27 Claims, 3 Drawing Sheets

PREFORMED BRACE FOR TREATING METACARPAL FRACTURES AND METHOD OF TREATING METACARPAL FRACTURES

This application claims the benefit of U.S. provisional patent application No. 60/405,627 filed on Aug. 22, 2002, which is incorporated herein and made a part hereof by reference.

BACKGROUND OF THE INVENTION

The present invention relates to the field of medical braces for treating metacarpal fractures. More specifically, the present invention relates to a preformed brace for immobilizing fractures of the metacarpal neck. The molded metacarpal fracture brace of the present invention is a functional brace designed specifically for the acute and sub-acute treatment of fractures involving the neck of the fourth and/or fifth metacarpal, the so-called "boxers fracture".

The "boxers fracture" is the most common type of hand fracture. The treatment of this type of fracture is controversial and ranges from no immobilization of the fracture at all to complete immobilization of the fracture for up to six weeks. Most orthopedic surgeons agree that some period of immobilization is required to achieve a favorable result.

There have been a number of methods that have been utilized to immobilize the fourth and fifth metacarpalphalangeal joints (i.e. knuckles). Historically the most common method has been splinting or casting the hand with plaster of Paris or fiberglass. Many studies have shown that the most favorable position to splint the metacarpalphalangeal joint is one at which the joint is placed at 90 degrees. This position places the ligaments around the joint in an elongated position during the period of immobilization, therefore preventing problems with finger extension once immobilization is removed. It has been shown that if the joint is immobilized in an extended position the ligaments may shorten, thus preventing adequate flexion when immobilization is removed. More recently there have been a number of braces designed to immobilize the fourth and/or fifth metacarpal. For example, U.S. Pat. No. 4,662,364 to Viegas discloses a splint (commonly known as the Galveston Metacarpal Brace™) which applies pressure directly over the fracture sight to provide immobilization while allowing full motion of the hand. Also, U.S. patent application Ser. No. 20020002348 to Wiggins discloses a "universal" brace which immobilizes the fracture in an "extension" position.

It would be advantageous to provide a preformed one-piece metacarpal fracture brace which firmly immobilizes the fourth and fifth metacarpal necks in a functional position at approximately 90 degrees. It would be further advantageous to provide a one-piece preformed metacarpal brace which is lightweight, comfortable, and adjustable to fit various sizes. It would be further advantageous if such a brace were made of material which could be further molded after heat treatment to provide further customizability.

The present invention provides the foregoing and other advantages.

SUMMARY OF THE INVENTION

The present invention relates to a pre-formed functional metacarpal fracture brace designed for the acute and sub-acute treatment of fractures involving the neck of the fourth and/or fifth metacarpal, the so-called "boxers fracture". The metacarpal fracture brace is the first type of metacarpal fracture brace that comes as a one-piece functional splint that firmly immobilizes the fourth and fifth metacarpal necks at approximately 90 degrees. The combination of a lightweight malleable plastic outer shell with a soft inner lining provides lightweight comfort and versatility. The unique strap design, together with the accompanying malleable plastic outer shell allows excellent compression over the fracture site.

In accordance with one example embodiment of the invention, a preformed metacarpal fracture brace is provided. The brace comprises a one-piece semi-rigid molded outer shell contoured to conform to an outside portion of a wrist and hand of a wearer. The outer shell may comprise a proximal section adapted to immobilize the wrist in an extension position and a distal section extending at an angle to the proximal section and adapted to immobilize at least the fourth and fifth metacarpals of the hand in a functional position at that angle. A soft inner shell may be applied to an inside portion of the outer shell. A plurality of straps connected to the outer shell may be provided to secure the brace onto the wearer.

In a further example embodiment, the outer shell may have a C-shaped cross-section. The outer shell may extend in a longitudinal direction from above the wearer's wrist to the tips of the wearer's fingers. The proximal section of the outer shell may extend in a direction transverse to the longitudinal direction at least from the outside portion of the wearer's wrist to approximately a midpoint of the wrist. The distal section of the outer shell may extend in the transverse direction at least from the outside portion of the wearer's hand over the fourth metacarpal. The outer shell may be open-ended along its width at a distal end and at a proximal end.

The angle at which the distal section extends may comprise an angle in the range between 80 to 90 degrees. Those skilled in the art will appreciate that the inventive brace may be manufactured so that the distal section extends at various angles (e.g., less than 80 degrees or more than 90 degrees).

The outer shell may be comprised of malleable plastic and may be formed using a vacuum molding process. The outer shell may be conformed to the contours of the wearer's wrist and hand by heat-treating the outer shell after the -brace is applied to the wearer. For example, the outer shell may be heated with a heat gun to allow the shell to be conformed to the contours of the wrist and hand of a wearer.

The outer shell of the brace may be trimmed to conform to a wearer's hand and wrist. In addition, the proximal portion of the outer shell may be adapted to be separated from the distal portion by cutting. This allows early motion of the wrist and allows the wearer to regain additional functionality while still providing immobilization to the fracture site.

The straps may comprise Velcro straps. A first strap may secure the brace above the wrist of the wearer. A second strap may secure the brace around a palm portion of the wearer's hand. A third strap may secure the brace around fingers of the wearer.

The present invention also includes a method for immobilizing metacarpal fractures using the above-described preformed metacarpal brace. In one example embodiment of the inventive method, a preformed metacarpal brace is applied to an injured hand and adjacent wrist. The metacarpal brace may comprise a one-piece semi-rigid molded outer shell contoured to conform to an outside portion of the wrist and hand. The outer shell may comprise a proximal section adapted to immobilize the wrist in an extension position and a distal section extending at an angle to the proximal section and adapted to immobilize at least the fourth and fifth metacarpals of the hand in a functional position at that angle. A soft inner shell may be applied to an inside portion of the outer shell. A plurality of straps connected to the outer shell may be provided to secure the brace onto the wearer. Once the brace is applied to the wrist and hand of the wearer, the brace may be tightened around the wrist and hand using the straps in order to secure the brace to the wearer and to immobilize the wrist and the fourth and fifth metacarpals.

Once the brace is applied, it can be further customized to conform to the particular contours of the wearer's wrist and hand. For example the outer shell may be heat treated in order to conform the outer shell to the contours of the wearer's wrist and hand. Further, the outer shell of the brace may be trimmed to conform the brace to a wearer's hand and wrist.

The proximal portion of the outer shell may be separated from the distal portion by cutting after a predetermined initial healing period. The proximal portion of the brace may then be removed in order to allow wrist movement while maintaining immobilization of the fourth and fifth metacarpals.

The brace may be secured to wearer's wrist and hand by tightening a first strap to secure the brace above the wrist of the wearer. A second strap may be tightened to secure the brace around a palm portion of the wearer's hand. A third strap may be tightened to secure the brace around fingers of the wearer. Those skilled in the art will appreciate that additional straps may be provided, for example if a brace with a longer proximal section is used.

The inventive brace can be used acutely for the immediate treatment of the "boxers fracture" in the emergency room setting or it can be applied in the physicians office several weeks after an initial predetermined healing period of cast or splint immobilization. Some physicians may feel more confident with initial splint or cast immobilization until the fracture starts to heal. In this situation the preformed brace would play a "transitional role" until the fracture is totally healed.

BRIEF DESCRIPTION OF THE DRAWINGS

The present invention will hereinafter be described in conjunction with the appended drawing figures, wherein like numerals denote like elements, and.

DETAILED DESCRIPTION OF THE INVENTION

The ensuing detailed description provides exemplary embodiments only, and is not intended to limit the scope, applicability, or configuration of the invention. Rather, the ensuing detailed description of the exemplary embodiments will provide those skilled in the art with an enabling description for implementing the invention. It should be understood that various changes may be made in the function and arrangement of elements without departing from the spirit and scope of the invention as set forth in the appended claims.

As shown in FIGS. 1–6, the metacarpal fracture brace 10 of the present invention is a one-piece functional splint that firmly immobilizes the fourth and fifth metacarpal necks in a functional position. The combination of a lightweight malleable plastic outer shell 12 with a soft inner lining 14 provides lightweight comfort and versatility. As shown in the Figures, the outer shell 12 is molded to approximately conform to the outer contours of the human hand and wrist, so that the wrist is held in extension and the fourth and fifth metacarpals are immobilized in a functional position (e.g., at approximately 90 degrees).

Figure 3:
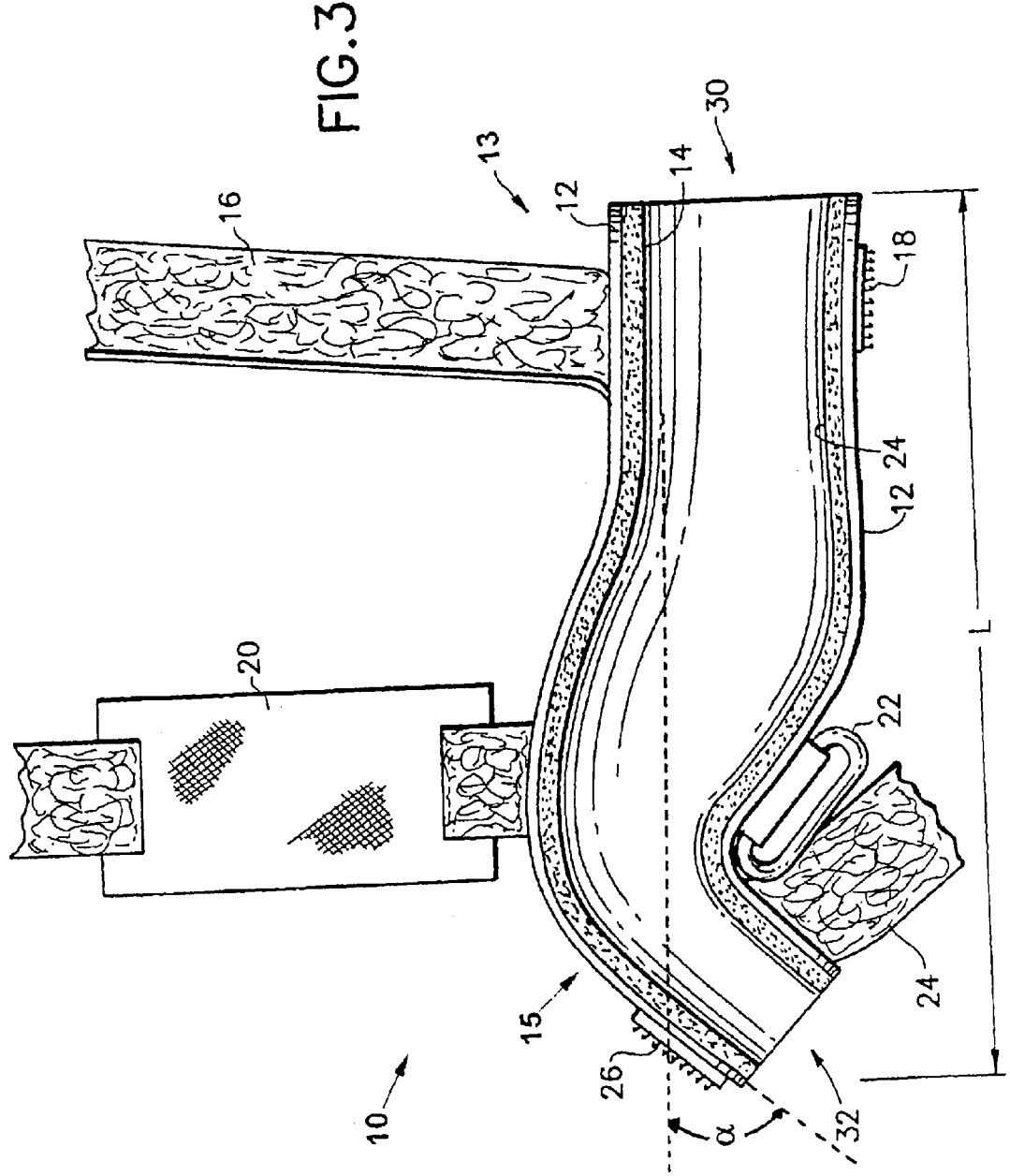
FIG. 3 shows a side view of an example embodiment of the inventive brace.

In an example embodiment of the invention, the brace comprises a one-piece semi-rigid molded outer shell 12 contoured to conform to an outside portion of a wrist 50 and hand of a wearer 55. As shown in FIG. 3, the outer shell 12 may comprise a proximal section 13 adapted to immobilize the wrist in an extension position and a distal section 15 extending at an angle $\alpha$ to the proximal section and adapted to immobilize at least the fourth and fifth metacarpals of the hand 55 in a functional position at the angle $\alpha$. A soft inner shell or lining 14 may be applied to an inside portion of the outer shell 12. A plurality of straps 16, 20, and 24 connected to the outer shell 12 may be provided to secure the brace 10 onto the wearer.

The proximal section 13 of the outer shell 12 may extend in a direction transverse to the longitudinal direction L at least from the outside portion of the wearer's wrist 50 to approximately a midpoint of the wrist 50. The distal section 15 of the outer shell 12 may extend in the transverse direction at least from the outside portion of the wearer's hand 55 over the fourth metacarpal, as shown for example in FIGS. 1, 2, and 6.

The angle $\alpha$ at which the distal section 15 extends may comprise an angle in the range between 80 to 90 degrees. Those skilled in the art will appreciate that the inventive brace may be manufactured so that the distal section 15 extends at various angles to the proximal section 13 (e.g., less than 80 degrees or more than 90 degrees).

Figure 1:
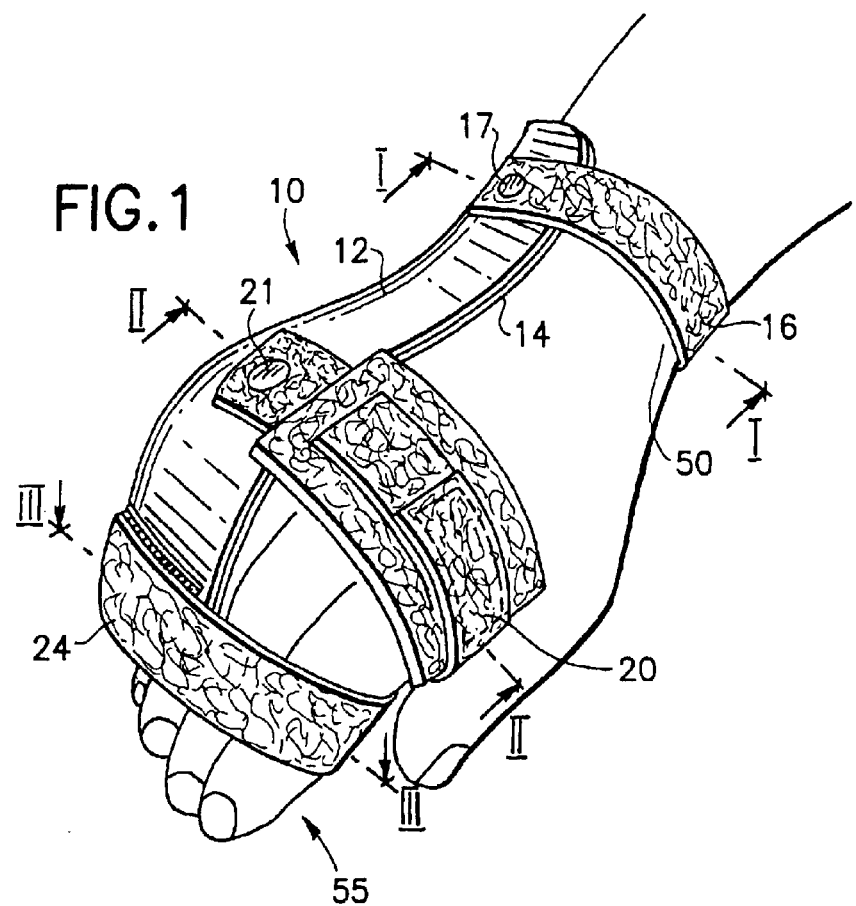
FIG. 1 shows a perspective view of an example embodiment of the inventive brace as fitted to a patient.
Figure 2:
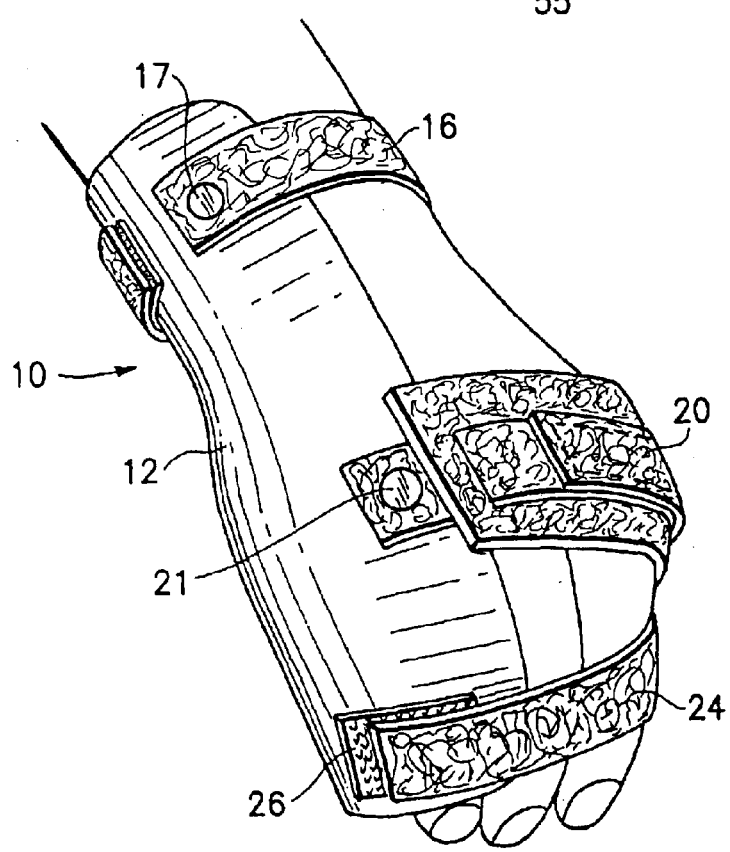
FIG. 2 shows a further perspective view of an example embodiment of the inventive brace as fitted to a patient.
Figure 4:
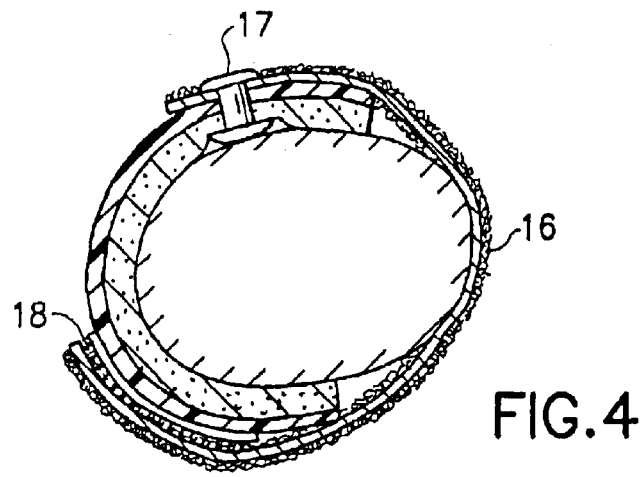
FIG. 4 shows a sectional view of an example embodiment of the inventive brace along section line I—I of FIG. 1.
Figure 5:
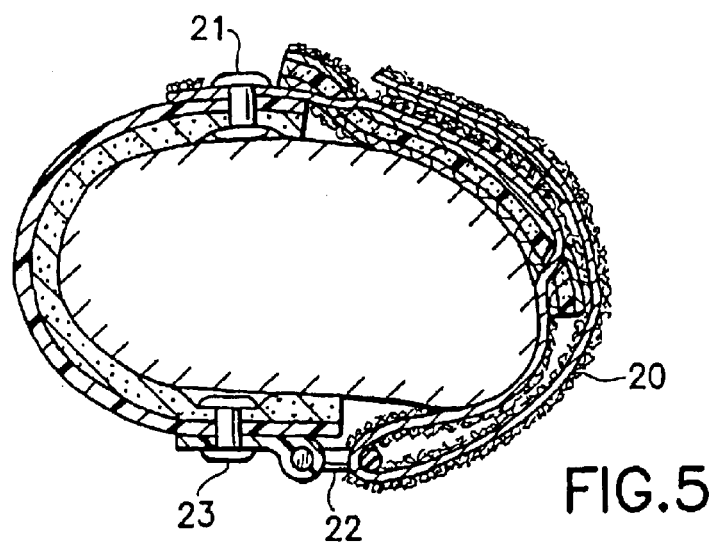
FIG. 5 shows a sectional view of an example embodiment of the inventive brace along section line II—II of FIG. 1.
Figure 6:
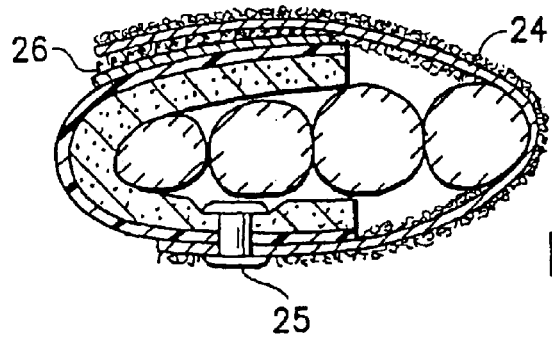
FIG. 6 shows a sectional view of an example embodiment of the inventive brace as fitted to a patient along sectional line III—III of FIG. 1.

As shown in FIGS. 1–3, the brace is open ended along its length L, which extends in a longitudinal direction from the above the wrist 50 of the wearer to the tips of the fingers of the hand 55. The brace 10 is also open along its width at its proximal end 30 and its distal end 32. The brace therefore has an approximately C-shaped cross section along its length L, as can be seen in FIGS. 4–6.

The outer shell 12 may be formed from a malleable plastic. The strap design, together with accompanying malleable plastic outer shell 12, allows for excellent compression over the fracture site. A plurality of straps 16, 20, and 24 are provided for securing the brace 10 to the wearer. The straps 16, 20, and 24 may be Velcro straps, one end of which may be secured to the outer shell 12 using a rivet, a screw, or other suitable fastening device.

For example, strap 16 secures the brace 10 above the wrist 50 of the wearer. One end of strap 16 is secured to the brace via rivet 17. The other end of strap 16 is secured to the brace 10 via a corresponding Velcro pad 18 which may be glued to the outer shell 12. Strap 20 secures the brace 10 around the palm of the hand 55. One end of strap 20 is secured to the outer shell via a rivet 21. The other end of the strap 20 is passed through a loop or ring 22 and secured back onto itself (e.g., using Velcro). The ring or loop 22 may comprise plastic, metal or other suitable material, which may be secured to the outer shell 12 using a rivet 23. The strap 24 secures the brace around the fingers 55 of the wearer. One end of strap 24 is secured to the outer shell 12 via a rivet 25. The other end of strap 24 is secured to the brace 10 via a corresponding Velcro pad 26 which may be glued to the outer shell 12.

The figures show three straps 16, 20, and 24. Those skilled in the art will appreciate that a different number or configuration of the straps and corresponding fastening devices may be employed without altering the character of the invention.

The Figures show a right-handed version of the inventive brace. Those skilled in the art will appreciate that the brace may be manufactured in both left and right-hand models, as well as in varying sizes, such as small, medium, large and extra-large. Further, the brace may be manufactured in varying lengths L.

The material of the outer shell 12 of the brace 10 may be heated (e.g., using a heat gun) such that the brace 10 may then be further molded around the fracture site. In this manner, the brace 10 may be customized so that it more closely conforms to the particular wearer's wrist and hand. The brace may also be trimmed for further customization.

In addition, the most proximal portion (e.g., in the region between straps 16 and 20) of the brace 10 can be cut and separated from the distal section 15 to allow early motion of the wrist 50. This allows the wearer to regain additional functionality while still providing immobilization to the fracture site.

The brace 10 can be used acutely for the immediate treatment of the "boxers fracture" in the emergency room setting or it can be applied in the physicians office several weeks after a period of cast or splint immobilization. Alternatively, the brace may be applied after the predetermined initial healing period during which the hand and wrist are immobilized using a splint or cast. In this situation the brace of the present invention would play a "transitional role" until the fracture is totally healed.

It should now be appreciated that the present invention provides an advantageous brace for immobilizing metacarpal fractures, as well as advantageous methods for immobilizing metacarpal fractures using the inventive brace.

Although the invention has been described in connection with various illustrated embodiments, numerous modifications and adaptations may be made thereto without departing from the spirit and scope of the invention as set forth in the claims.

What is claimed is:

1. A preformed metacarpal fracture brace, comprising:
   a one-piece semi-rigid molded outer shell contoured to conform to an outside portion of a wrist and hand of a wearer, said outer shell comprising a proximal section adapted to immobilize the wrist in an extension position and a distal section extending at an angle to the proximal section and adapted to immobilize at least the fourth and fifth metacarpals of the hand in a functional position at said angle;
   a soft inner shell applied to an inside portion of said outer shell; and
   a plurality of straps connected to said outer shell adapted to secure said brace onto said wearer; wherein:
   said outer shell extends in a longitudinal direction from above the wearer's wrist to the tips of the wearer's fingers;
   said proximal section of said outer shell extends in a direction transverse to the longitudinal direction at least from the outside portion of the wearer's wrist to approximately a midpoint of the wrist; and
   said distal section of said outer shell extends in said transverse direction at least from the outside portion of the wearer's hand over said fourth metacarpal.

2. A brace in accordance with claim 1, wherein said outer shell has a C-shaped cross-section.

3. A brace in accordance with claim 2, wherein said outer shell is open-ended along its width at a distal end and at a proximal end.

4. A brace in accordance with claim 1, wherein said angle comprises an angle in the range between 80 to 90 degrees.

5. A brace in accordance with claim 1, wherein said outer shell is comprised of plastic which is malleable after heat-treating.

6. A brace in accordance with claim 1, wherein said straps comprise Velcro straps.

7. A brace in accordance with claim 1, wherein:
   a first strap secures the brace above the wrist of the wearer;
   a second strap secures the brace around a palm portion of the wearer's hand; and
   a third strap secures the brace around fingers of the wearer.

8. A preformed metacarpal fracture brace, comprising:
   a one-piece semi-rigid molded outer shell contoured to conform to an outside portion of a wrist and hand of a wearer, said outer shell comprising a proximal section adapted to immobilize the wrist in an extension position and a distal section extending at an angle to the proximal section and adapted to immobilize at least the fourth and fifth metacarpals of the hand in a functional position at said angle;
   a soft inner shell applied to an inside portion of said outer shell; and
   a plurality of straps connected to said outer shell adapted to secure said brace onto said wearer;
   wherein said outer shell is conformed to the contours of the wearer's wrist and hand by heat-treating said outer shell after said brace is applied to said wearer.

9. A brace in accordance with claim 8, wherein said outer shell extends in a longitudinal direction from above the wearer's wrist to the tips of the wearer's fingers.

10. A brace in accordance with claim 9, wherein:
    said proximal section of said outer shell extends in a direction transverse to the longitudinal direction at least from the outside portion of the wearer's wrist to approximately a midpoint of the wrist; and
    said distal section of said outer shell extends in said transverse direction at least from the outside portion of the wearer's hand over said fourth metacarpal.

11. A brace in accordance with claim 8, wherein said outer shell is formed using a vacuum molding process.

12. A preformed metacarpal fracture brace, comprising:
    a one-piece semi-rigid molded outer shell contoured to conform to an outside portion of a wrist and hand of a wearer, said outer shell comprising a proximal section adapted to immobilize the wrist in an extension position and a distal section extending at an angle to the proximal section and adapted to immobilize at least the fourth and fifth metacarpals of the hand in a functional position at said angle;
    a soft inner shell applied to an inside portion of said outer shell; and a plurality of straps connected to said outer shell adapted to secure said brace onto said wearer;
wherein said outer shell of said brace is adapted to be trimmed to conform to a wearer's hand and wrist.

13. A brace in accordance with claim 12, wherein the proximal portion of the outer shell is adapted to be separated from the distal portion by cutting.

14. A method of treating metacarpal fractures, comprising:
applying a preformed metacarpal brace to an injured hand and adjacent wrist, said metacarpal brace comprising:
a one-piece semi-rigid molded outer shell contoured to conform to an outside portion of the wrist and hand, said outer shell comprising a proximal section adapted to immobilize the wrist in an extension position and a distal section extending at an angle to the proximal section and adapted to immobilize at least the fourth and fifth metacarpals of the hand in a functional position at said angle;
a soft inner shell applied to an inside portion of said outer shell; and
a plurality of straps connected to said outer shell adapted to secure said brace onto a wearer;
trimming said outer shell of said brace to conform the brace to a wearer's hand and wrist; and
tightening said brace around said wrist and hand using said straps in order to secure the brace to the wearer and to immobilize said wrist and said fourth and fifth metacarpals.

15. A method in accordance with claim 14, wherein said outer shell has a C-shaped cross-section.

16. A method in accordance with claim 15, wherein said outer shell extends in a longitudinal direction from above the wearer's wrist to the tips of the wearer's fingers.

17. A method in accordance with claim 15, wherein said outer shell is open-ended along its width at a distal end and at a proximal end.

18. A method in accordance with claim 14, wherein said angle comprises an angle in the range between 80 to 90 degrees.

19. A method in accordance with claim 14, wherein said outer shell is comprised of plastic which is malleable after heat-treating.

20. A method in accordance with claim 14, wherein said straps comprise Velcro straps.

21. A method in accordance with claim 14, further comprising:
separating the proximal portion of the outer shell from the distal portion by cutting after a predetermined initial healing period; and
removing the proximal portion of the brace in order to allow wrist movement while maintaining immobilization of the fourth and fifth metacarpals.

22. A method in accordance with comprising:
tightening a first strap to secure the brace above the wrist of the wearer;
tightening a second strap to secure the brace around a palm portion of the wearer's hand; and
tightening a third strap to secure the brace around fingers of the wearer.

23. A method in accordance with claim 14, wherein said brace is applied after a predetermined initial healing period during which the hand and wrist are immobilized using a cast.

24. A method of treating metacarpal fractures, comprising:
applying a preformed metacarpal brace to an injured hand and adjacent wrist, said metacarpal brace comprising:
a one-piece semi-rigid molded outer shell contoured to conform to an outside portion of the wrist and hand, said outer shell comprising a proximal section adapted to immobilize the wrist in an extension position and a distal section extending at an angle to the proximal section and adapted to immobilize at least the fourth and fifth metacarpals of the hand in a functional position at said angle;
a soft inner shell applied to an inside portion of said outer shell; and
a plurality of straps connected to said outer shell adapted to secure said brace onto a wearer; and
tightening said brace around said wrist and hand using said straps in order to secure the brace to the wearer and to immobilize said wrist and said fourth and fifth metacarpals;
wherein:
said outer shell extends in a longitudinal direction from above the wearer's wrist to the tips of the wearer's fingers;
said proximal section of said outer shell extends in a direction transverse to the longitudinal direction at least from the outside portion of the wearer's wrist to approximately a midpoint of the wrist; and
said distal section of said outer shell extends in said transverse direction at least from the outside portion of the wearer's hand over said fourth metacarpal.

25. A method of treating metacarpal fractures, comprising:
applying a preformed metacarpal brace to an injured hand and adjacent wrist, said metacarpal brace comprising:
a one-piece semi-rigid molded outer shell contoured to conform to an outside portion of the wrist and hand, said outer shell comprising a proximal section adapted to immobilize the wrist in an extension position and a distal section extending at an angle to the proximal section and adapted to immobilize at least the fourth and fifth metacarpals of the hand in a functional position at said angle;
a soft inner shell applied to an inside portion of said outer shell; and
a plurality of straps connected to said outer shell adapted to secure said brace onto a wearer;
heat-treating said outer shell to conform the outer shell to the contours of the wearer's wrist and hand; and
tightening said brace around said wrist and hand using said straps in order to secure the brace to the wearer and to immobilize said wrist and said fourth and fifth metacarpals.

26. A method in accordance with claim 25, further comprising trimming said outer shell of said brace to conform the brace to a wearer's hand and wrist.

27. A method in accordance with claim 25, wherein said outer shell is formed using a vacuum molding process.

* * * * *

UNITED STATES PATENT AND TRADEMARK OFFICE
CERTIFICATE OF CORRECTION

PATENT NO. : 6,953,441 B2 Page 1 of 1
DATED : October 11, 2005
INVENTOR(S) : Douglas M. Goumas It is certified that error appears in the above-identified patent and that said Letters Patent is hereby corrected as shown below:

<u>Column 7,</u>
Line 53, should read:
-- 22. A method in accordance with claim 14, further comprising: --.

Signed and Sealed this

Twentieth Day of December, 2005

JON W. DUDAS
*Director of the United States Patent and Trademark Office*